US009066936B2

(12) United States Patent
Yoneyama et al.

(10) Patent No.: US 9,066,936 B2
(45) Date of Patent: Jun. 30, 2015

(54) SOLID PHARMACEUTICAL COMPOSITION COMPRISING A BENZIMIDAZOLE-7-CARBOXYLATE DERIVATIVE AND A PH CONTROL AGENT

(75) Inventors: Shuji Yoneyama, Osaka (JP); Yutaka Tanoue, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/450,403

(22) PCT Filed: Mar. 26, 2008

(86) PCT No.: PCT/JP2008/056522
§ 371 (c)(1),
(2), (4) Date: Sep. 24, 2009

(87) PCT Pub. No.: WO2008/123536
PCT Pub. Date: Oct. 16, 2008

(65) Prior Publication Data
US 2010/0121071 A1    May 13, 2010

Related U.S. Application Data

(60) Provisional application No. 60/908,515, filed on Mar. 28, 2007.

(51) Int. Cl.
*A61K 31/4245* (2006.01)
*A61K 9/16* (2006.01)
*A61K 9/20* (2006.01)

(52) U.S. Cl.
CPC ........... *A61K 31/4245* (2013.01); *A61K 9/1676* (2013.01); *A61K 9/1682* (2013.01); *A61K 9/2009* (2013.01); *A61K 9/2013* (2013.01); *A61K 9/2027* (2013.01); *A61K 9/205* (2013.01); *A61K 9/2054* (2013.01); *A61K 9/2095* (2013.01)

(58) Field of Classification Search
CPC .................................. A61K 31/4245
USPC ....................................... 514/364
See application file for complete search history.

(56) References Cited

U.S. PATENT DOCUMENTS

| | | | | | |
|---|---|---|---|---|---|
| 5,196,444 | A | * | 3/1993 | Naka et al. | 514/381 |
| 5,250,554 | A | * | 10/1993 | Naka et al. | 514/381 |
| 5,328,919 | A | * | 7/1994 | Naka et al. | 514/381 |
| 5,401,764 | A | * | 3/1995 | Naka et al. | 514/381 |
| 5,508,297 | A | * | 4/1996 | Nishikawa | 514/381 |
| 5,534,534 | A | * | 7/1996 | Makino et al. | 514/388 |
| 5,583,141 | A | * | 12/1996 | Naka et al. | 514/303 |
| 5,605,919 | A | * | 2/1997 | Matsumori | 514/381 |
| 5,639,773 | A | * | 6/1997 | Kubo et al. | 514/382 |
| 5,705,517 | A | * | 1/1998 | Naka et al. | 514/381 |
| 5,719,173 | A | * | 2/1998 | Nishikawa et al. | 514/381 |
| 5,721,263 | A | * | 2/1998 | Inada et al. | 514/381 |
| 5,736,555 | A | * | 4/1998 | Naka et al. | 514/303 |
| 5,736,561 | A | * | 4/1998 | Nishikawa | 514/364 |
| 5,750,551 | A | * | 5/1998 | Matsumori | 514/381 |
| 5,889,036 | A | * | 3/1999 | Nishikawa et al. | 514/381 |
| 5,958,961 | A | * | 9/1999 | Inada et al. | 514/394 |
| 5,962,491 | A | * | 10/1999 | Naka et al. | 514/381 |
| 6,004,989 | A | * | 12/1999 | Naka et al. | 514/381 |
| 6,040,324 | A | * | 3/2000 | Nishikawa et al. | 514/381 |
| 6,100,252 | A | * | 8/2000 | Naka et al. | 514/211.08 |
| 6,107,323 | A | * | 8/2000 | Tamura et al. | 514/401 |
| 6,228,874 | B1 | * | 5/2001 | Inada et al. | 514/364 |
| 6,232,334 | B1 | * | 5/2001 | Naka et al. | 514/381 |
| 6,319,938 | B1 | * | 11/2001 | Nishikawa et al. | 514/381 |
| 6,348,481 | B2 | * | 2/2002 | Inada et al. | 514/364 |
| 6,355,808 | B2 | * | 3/2002 | Naka et al. | 548/252 |
| 6,420,405 | B2 | * | 7/2002 | Inada et al. | 514/381 |
| 6,432,996 | B1 | * | 8/2002 | Tamura et al. | 514/401 |
| 6,469,037 | B2 | * | 10/2002 | Nishikawa et al. | 514/361 |
| 6,589,547 | B1 | * | 7/2003 | Igari et al. | 424/426 |
| 6,686,383 | B2 | * | 2/2004 | Nishikawa et al. | 514/381 |
| 6,833,381 | B2 | * | 12/2004 | Ikeya et al. | 514/397 |
| 6,852,743 | B1 | * | 2/2005 | Ojima et al. | 514/364 |
| 7,064,141 | B1 | * | 6/2006 | Nakagawa et al. | 514/381 |
| 7,135,490 | B2 | * | 11/2006 | Nishikawa et al. | 514/381 |
| 7,153,972 | B2 | * | 12/2006 | Naka et al. | 548/252 |
| 7,157,584 | B2 | * | 1/2007 | Kuroita et al. | 548/132 |
| 7,294,344 | B2 | * | 11/2007 | Igari et al. | 424/426 |
| 7,378,108 | B1 | * | 5/2008 | Iga et al. | 424/443 |
| 7,538,133 | B2 | * | 5/2009 | Naka et al. | 514/381 |
| 7,572,920 | B2 | * | 8/2009 | Kuroita et al. | 548/132 |
| 7,582,662 | B2 | * | 9/2009 | Terashita et al. | 514/364 |
| 7,588,779 | B2 | * | 9/2009 | Hahn | 424/464 |
| 7,812,044 | B2 | * | 10/2010 | Kubota et al. | 514/381 |
| 7,875,637 | B2 | * | 1/2011 | Kuroita et al. | 514/364 |
| 2006/0159747 | A1 | | 7/2006 | Schumacher et al. | |
| 2006/0177506 | A1 | * | 8/2006 | Yanai et al. | 424/468 |
| 2008/0279942 | A1 | | 11/2008 | Hamaura et al. | |
| 2009/0208583 | A1 | | 8/2009 | Rohrich et al. | |
| 2009/0214664 | A1 | | 8/2009 | Ohm et al. | |
| 2009/0306151 | A1 | | 12/2009 | Hamaura et al. | |
| 2010/0204252 | A1 | * | 8/2010 | Kupfer | 514/264.1 |
| 2011/0281823 | A1 | | 11/2011 | Hamaura et al. | |

FOREIGN PATENT DOCUMENTS

| | | |
|---|---|---|
| EP | 1 258 254 A1 | 11/2002 |
| EP | 1 452 176 A1 | 9/2004 |
| EP | 1 787 647 A1 | 5/2007 |
| WO | WO 2004082679 A1 * | 9/2004 |
| WO | WO 2005/080384 A3 | 9/2005 |
| WO | WO 2006/124713 A3 | 11/2006 |
| WO | WO 2007/001066 A1 | 1/2007 |
| WO | WO 2007/003330 A2 | 1/2007 |
| WO | WO 2008/045006 A1 | 4/2008 |
| WO | WO 2008/068217 A2 | 6/2008 |

OTHER PUBLICATIONS

Kubo et al. J. Med. Chem. 1993, 36, 2343-2349.*
Sakamoto et al. Chem. Pharm. Bull. 1984, 32, 2241-2248.*
International Search Report mailed Jul. 29, 2008 in prior PCT/JP2008/056522, four pages.

* cited by examiner

*Primary Examiner* — Joseph Kosack
*Assistant Examiner* — Matthew Coughlin
(74) *Attorney, Agent, or Firm* — Foley & Lardner LLP (57) ABSTRACT

The present invention provides a solid pharmaceutical composition containing compound (I) having an angiotensin II receptor antagonistic action and defined in the specification and a pH control agent, which composition is superior in the stability and dissolution property of compound (I).

3 Claims, 2 Drawing Sheets

SOLID PHARMACEUTICAL COMPOSITION COMPRISING A BENZIMIDAZOLE-7-CARBOXYLATE DERIVATIVE AND A PH CONTROL AGENT

CROSS-REFERENCE TO RELATED APPLICATIONS

This application is a National Stage application of PCT/JP2008/056522, filed Mar. 26, 2008, which claims priority from U.S. Provisional Application No. 60/908,515, filed Mar. 28, 2007.

TECHNICAL FIELD OF THE INVENTION

The present invention relates to a solid pharmaceutical composition comprising the below-mentioned compound (I) and a pH control agent, which is superior in both the stability and dissolution property of compound (I). In addition, the present invention relates to a method of stabilizing compound (I) and a method of improving dissolution of compound (I).

BACKGROUND OF THE INVENTION

It is important that pharmaceutical products be effective and safe. Even if a pharmaceutical product is effective and safe immediately after production, if the drug is easily decomposed or denatured during distribution, it is not effective and safe as a pharmaceutical product. Therefore, the stability of the drug is extremely important for pharmaceutical products.

In addition, to maintain effectiveness and safety of a pharmaceutical product, not only the effectiveness and safety of the active ingredient but also the properties of the pharmaceutical preparation, such as drug dissolution property in the body and the like, are extremely important. For example, when dissolution of the drug from the pharmaceutical preparation is too slow, the blood concentration of the drug does not reach an effective level, and the expected efficacy may not be sufficiently exhibited. On the other hand, when dissolution of the drug from the pharmaceutical preparation is too fast, the blood concentration of the drug increases rapidly, and the risk of side effects increases.

In other words, a pharmaceutical product is required to ensure stability and constant dissolution of drug, in addition to the effectiveness and safety.

Meanwhile, drug dissolution property is known to correlate to the solubility of a drug. That is, it is known that, in general, a lower solubility of a drug is associated with slower drug dissolution property.

Incidentally, benzimidazole derivative (I) having a strong angiotensin II receptor antagonistic activity (I)

wherein $R^1$ is a monocyclic nitrogen-containing heterocyclic group having a hydrogen atom that can be deprotonized, $R^2$ is an esterified carboxyl group, and $R^3$ is an optionally substituted lower alkyl, or a salt thereof (hereinafter to be sometimes referred to as compound (I)), particularly, a salt of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate (WO2005/080384) is a promising therapeutic drug for hypertension and the like.

However, the properties of a pharmaceutical preparation need to be adjusted to stabilize compound (I) because compound (I) is unstable in the neutral pH range, at which pharmaceutical preparations are generally produced. Nevertheless, the solubility of compound (I) is low at a pH range where compound (I) is stable.

It is therefore extremely difficult to simultaneously afford the stability and solubility of compound (I), and simultaneous achievement thereof is desired.

DISCLOSURE OF THE INVENTION

An object of the present invention is to provide a solid pharmaceutical composition superior both in the stability and dissolution property of compound (I).

Another object of the present invention is to provide a method of stabilizing compound (I), and further, a method of improving dissolution thereof.

The present inventors have conducted intensive studies in an attempt to simultaneously achieve the stability of compound (I) in a preparation and dissolution property thereof from the preparation and found that the objects can be unexpectedly accomplished by the co-presence of a pH control agent and compound (I), and further, by adjusting, with a pH control agent, the pH range of a solid preparation thereof to a pH range in which the solubility of compound (I) becomes low, which resulted in the completion of the present invention.

Accordingly, the present invention provides the following.
(1) A solid pharmaceutical composition comprising a compound represented by the formula (I)

(I)

wherein $R^1$ is a monocyclic nitrogen-containing heterocyclic group having a hydrogen atom that can be deprotonized, $R^2$ is an esterified carboxyl group, and $R^3$ is an optionally substituted lower alkyl, or a salt thereof, and a pH control agent.
(2) The pharmaceutical composition of the aforementioned (1), wherein the salt of the compound represented by the formula (I) is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt (hereinafter to be sometimes referred to as compound A).
(3) The pharmaceutical composition of the aforementioned (1) or (2), wherein the pH control agent has pH 2 to 5.
(4) The pharmaceutical composition of the aforementioned (3), wherein the pH control agent is monosodium fumarate or a combination of fumaric acid and sodium hydroxide.
(5) A method of stabilizing a compound represented by the formula (I) or a salt thereof in a solid pharmaceutical composition, which comprises adding a pH control agent to the solid pharmaceutical composition comprising the compound represented by the formula (I) or a salt thereof.

(6) A method of improving dissolution of a compound represented by the formula (I) or a salt thereof from a solid pharmaceutical composition, which comprises adding a pH control agent to the solid pharmaceutical composition comprising the compound represented by the formula (I) or a salt thereof.

(7) Use of a pH control agent for stabilizing a compound represented by the formula (I) or a salt thereof in a solid pharmaceutical composition comprising the compound represented by the formula (I) or a salt thereof.

(8) Use of a pH control agent for improving the dissolution property of a compound represented by the formula (I) or a salt thereof from a solid pharmaceutical composition comprising the compound represented by the formula (I) or a salt thereof.

The solid pharmaceutical composition of the present invention is superior in the stability of compound (I) contained therein, as well as the dissolution property of the compound.

According to the stabilizing method of compound (I) of the present invention, moreover, compound (I) in a solid pharmaceutical composition is significantly stabilized. Furthermore, according to the method of improving dissolution of compound (I), the dissolution property of the compound (I) from a solid pharmaceutical composition can be significantly improved.

DETAILED DESCRIPTION OF THE INVENTION

In the aforementioned formula (I), $R^1$ is a monocyclic nitrogen-containing heterocyclic group having a hydrogen atom that can be deprotonized, such as a tetrazolyl group or a group represented by the formula wherein i is —O— or —S—, j is >C=O, >C=S or >S(O)m wherein m is 0, 1 or 2 (e.g., 4,5-dihydro-5-oxo-1,2,4-oxadiazol-3-yl group, etc.) and the like are preferable.

A 4,5-dihydro-5-oxo-1,2,4-oxadiazol-3-yl group includes three tautomers (a', b' and c') represented by the formulas:

and 4,5-dihydro-5-oxo-1,2,4-oxadiazol-3-yl group includes all of the above-mentioned a', b' and c'.

In the aforementioned formula (I), $R^2$ is an esterified carboxyl group and, for example, preferably a carboxyl group esterified by lower ($C_{1-4}$)alkyl optionally substituted by a substituent selected from a hydroxyl group, an amino group, a halogen atom, lower ($C_{2-6}$)alkanoyloxy (e.g., acetyloxy, pivaloyloxy, etc.), lower ($C_{4-7}$)cycloalkanoyloxy, (lower ($C_{1-6}$) alkoxy)carbonyloxy (e.g., methoxycarbonyloxy, ethoxycarbonyloxy, etc.), (lower ($C_{3-7}$)cycloalkoxy)carbonyloxy (e.g., cyclohexyloxycarbonyloxy, etc.), lower ($C_{1-4}$) alkoxy and 5-methyl-2-oxo-1,3-dioxolene-4-yl (e.g., (5-methyl-2-oxo-1,3-dioxolen-4-yl)methoxycarbonyl group, 1-(cyclohexyloxycarbonyloxy)ethoxycarbonyl group) and the like.

In the aforementioned formula (I), $R^3$ is an optionally substituted lower alkyl, and preferably a lower ($C_{1-5}$)alkyl optionally substituted by a substituent selected from a hydroxyl group, an amino group, a halogen atom and a lower ($C_{1-4}$)alkoxy group (preferably lower ($C_{2-3}$)alkyl; particularly preferably ethyl).

As a salt of the compound represented by the formula (I), a pharmaceutically acceptable salt can be mentioned and, for example, a salt of a compound represented by the formula (I) with an inorganic base, a salt thereof with an organic base and the like can be mentioned. Preferable examples of the salt with an inorganic base include alkali metal salt such as sodium salt, potassium salt and the like; alkaline earth metal salt such as calcium salt, magnesium salt and the like; aluminum salt, ammonium salt and the like. Preferable examples of the salt with an organic base include salts with trimethylamine, triethylamine, pyridine, picoline, ethanolamine, diethanolamine, triethanolamine, dicyclohexylamine, N,N'-dibenzylethylenediamine and the like.

As a salt with a compound represented by the formula (I), an alkali metal salt of a compound represented by the formula (I) is preferable. Particularly, potassium salt of a compound represented by the formula (I) is preferable.

As a compound represented by the formula (I) or a salt thereof, a salt of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate is preferable, and (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt is particularly preferable.

The salt of a compound represented by the formula (I) may be hydrate or non-hydrate.

As the pH control agent to be used in the present invention, any pH control agent can be used as long as it can simultaneously achieve the stability of compound (I) in a drug product and dissolution property thereof from the drug product, and is applicable to pharmaceutical products. Plural pH control agents may be used in combination. As the pH control agent to be used in the present invention, a pH control agent showing pH of about 2 to about 5, preferably about 3 to about 5, more preferably about 3 to about 4 is preferably used. For example, an acidic substance such as tartaric acid, citric acid, lactic acid, fumaric acid, malic acid, ascorbic acid, acetic acid, acidic amino acid (e.g., glutamic acid, aspartic acid) and the like, inorganic salts of these acidic substances (e.g., alkali metal salt, alkaline earth metal salt, ammonium salt, etc.), salts of these acidic substances with an organic base (e.g., basic amino acid such as lysine, arginine, etc., meglumine, etc.), and a hydrate thereof, a solvate thereof and the like are used.

Here, the pH of the pH control agent is measured under the following conditions. To be precise, it is a pH of a solution or suspension obtained by dissolving or suspending a pH control agent in water at a concentration of 1% w/v at 25° C.

As the pH control agent to be used in the present invention, an acidic substance and a basic substance are combined, and the obtained pH control agent may be adjusted such that the pH of a solution or suspension is about 2 to about 5, preferably about 3 to about 5, more preferably about 3 to about 4, when the combined pH control agent is dissolved or suspended in water at 25° C. at a concentration of 1% w/v. Examples of the acidic substance to be used in combination include, in addition to the acidic substances having a pH of about 2 to about 5 mentioned above and salts thereof, strong acids such as hydrochloric acid, sulfuric acid, phosphoric acid and like. Examples of the basic substance to be used in combination include inorganic bases (e.g., sodium hydroxide, potassium hydroxide, sodium carbonate, sodium hydrogencarbonate, magnesium carbonate, calcium carbonate, magnesium oxide, ammonia, synthetic hydrotalcite), organic bases (e.g., basic amino acid such as lysine, arginine, etc., meglumine, and the like) and the like.

Furthermore, preferable examples of the pH control agent to be used in the present invention include those whose solutions have a buffering ability at said pH, such as sodium dihydrogen phosphate, monosodium fumarate and the like.

As the pH control agent to be used in the present invention, monosodium fumarate is particularly preferable, and fumaric acid and sodium hydroxide may be used in combination.

The solid pharmaceutical composition of the present invention contains a pH control agent at a proportion of 0.01-20 wt %, preferably 0.05-10 wt %, more preferably 0.1-5 wt %. Furthermore, the active ingredient, i.e., compound (I), is contained in the solid pharmaceutical composition at a proportion of 0.1-60 wt %, preferably 1-40 wt %, more preferably 10-30 wt %.

The solid pharmaceutical composition of the present invention may be used in the form of a solid drug product suitable for oral administration, such as tablet, granule, fine granule, capsule, pill and the like.

The solid preparation can be produced according to a method known per se (e.g., the method described in the General Rules for Preparations, The Japanese Pharmacopoeia 14th Edition). For example, when tablets are to be prepared, compound (I), a pH control agent, an excipient (e.g., lactose, sucrose, glucose, starch, cornstarch, saccharose, microcrystalline cellulose, powdered glycyrrhiza, mannitol, sorbitol, sodium hydrogen carbonate, calcium phosphate, calcium sulfate, calcium silicate, etc.), a disintegrant (e.g., amino acid, starch, cornstarch, calcium carbonate, carmellose sodium, carmellose calcium, croscarmellose sodium, low-substituted hydroxypropylcellulose, crospovidone, sodium carboxymethyl starch, etc.) and the like are combined; a binder (e.g., hydroxypropylcellulose, hydroxypropylmethylcellulose, polyvinylpyrrolidone, gelatin, starch, gum arabic, tragacanth, carboxymethylcellulose, sodium alginate, pullulan, glycerol, etc.) is added to give granules; a lubricant (e.g., magnesium stearate, stearic acid, calcium stearate, purification talc, etc.) and the like are added thereto; and the mixture is compressed to give tablets. Moreover, granules and fine granules are produced by granulation in the same manner as for tablets, or produced by coating Nonpareil (trade name, spherical granules containing sucrose 75% (W/W) and cornstarch 25% (W/W)) with, while spraying water or a solution of a binder such as sucrose, hydroxypropylcellulose, hydroxypropylmethylcellulose and the like (concentration: about 0.5-70% (W/V)), a dusting powder containing compound (I), a pH control agent and an additive (e.g., sucrose, cornstarch, microcrystalline cellulose, hydroxypropylcellulose, methylcellulose, polyvinylpyrrolidone, etc.). Capsules are produced by filling capsules made of gelatin, hydroxypropylmethylcellulose and the like with the above-mentioned granules or fine granules, or filling capsules made of gelatin, hydroxypropylmethylcellulose and the like with the active ingredient together with an excipient (e.g., lactose, sucrose, glucose, starch, saccharose, microcrystalline cellulose, powdered glycyrrhiza, mannitol, sodium hydrogencarbonate, calcium phosphate, calcium sulfate, etc.).

The solid preparation may be coated with a coating agent for masking of taste, enteric or sustained-release and the like. Examples of the coating agent include hydroxypropylmethylcellulose, ethylcellulose, hydroxymethylcellulose, hydroxypropylcellulose, polyoxyethyleneglycol, Tween 80, pluronic F68, cellulose acetate phthalate, hydroxypropylmethylcellulose phthalate, hydroxymethylcellulose acetate succinate, Eudragit (methacrylic acid acrylic acid copolymer, manufactured by Rohm, West Germany) and the like, and where necessary, a light shielding agent such as titanium oxide, red iron oxide and the like can also be used.

The solid pharmaceutical composition of the present invention can be safely used as a pharmaceutical agent for mammals (e.g., human, dog, rabbit, rat, mouse, etc.).

While the dose of compound (I) to patients is determined in consideration of age, body weight, general health condition, sex, diet, administration time, clearance rate, combination of drugs and the like, as well as the severity of the disease for which the patient is undergoing treatments, the daily dose is about 0.05-500 mg, preferably 0.1-100 mg.

EXAMPLES

While the following Examples explain the present invention in detail, they are not to be construed as limiting the present invention.

In the Examples and Comparative Examples, as lactose, mannitol, hydroxypropylcellulose, microcrystalline cellulose, low-substituted hydroxypropylcellulose, polyvinylpyrrolidone, purified sucrose, cornstarch and magnesium stearate, products compatible with the Japanese Pharmacopoeia 14th Edition were used, and as croscarmellose sodium, sucrose starch spherical granule and calcium silicate, Japanese Pharmaceutical Excipients 2003 compatible products were used.

Example 1

Compound A (1200 g) and mannitol (2673 g) were uniformly mixed in a fluid bed granulator (FD-5S, POWREX CORPORATION), and the mixture was granulated while spraying an aqueous solution of hydroxypropylcellulose (151.2 g), fumaric acid (56.00 g) and sodium hydroxide (19.32 g) and dried in the fluid bed granulator. The obtained granules were pulverized using a powermill grinder (P-3, Showa Chemical Machinery) and a 1.5 mmϕ punching screen. To the obtained milled granules (3660 g) were added croscarmellose sodium (345.0 g), microcrystalline cellulose (450.0 g) and magnesium stearate (45.00 g), and they were mixed in a tumbler mixer (TM-15, Showa Chemical Machinery). The obtained mixture was tableted by a rotary tableting machine (AQUARIUS, Kikusui Seisakusho, Ltd.) using a 9.5 mmϕ punch (tableting pressure: 6.5 KN/punch, weight per tablet: 360 mg) to give a plain tablet having the following composition. Then, the plain tablet was dried under reduced pressure at 40° C. for 16 hr.

Composition of Preparation (Per 360 mg)

| compound A | 85.36 mg |
| mannitol | 191.26 mg |
| hydroxypropylcellulose | 10.8 mg |
| fumaric acid | 4 mg |
| sodium hydroxide | 1.38 mg |
| croscarmellose sodium | 27.6 mg |
| microcrystalline cellulose | 36 mg |
| magnesium stearate | 3.6 mg |
| Total | 360 mg |

Example 2

Compound A (42.68 g), lactose (217.32 g), microcrystalline cellulose (32 g) and monosodium fumarate (10 g) were uniformly mixed in a fluid bed granulator (Lab-1, POWREX CORPORATION), and the mixture was granulated while spraying an aqueous solution of hydroxypropylcellulose (12 g) and monosodium fumarate (10 g) and dried in the fluid bed granulator to give granules.

Composition of Granules (Per 162 mg)

| compound A | 21.34 mg |
| lactose | 108.66 mg |
| microcrystalline cellulose | 16 mg |
| hydroxypropylcellulose | 6 mg |
| monosodium fumarate | 10 mg |
| Total | 162 mg |

Example 3

Compound A (42.68 g), lactose (217.32 g), microcrystalline cellulose (32 g) and monosodium fumarate (10 g) were uniformly mixed in a fluid bed granulator (Lab-1, POWREX CORPORATION), and the mixture was granulated while spraying an aqueous solution of hydroxypropylcellulose (12 g) and monosodium fumarate (10 g) and dried in the fluid bed granulator. The obtained granules were passed through 16 mesh sieves (aperture 1.0 mm) to give sieved granules. The obtained sieved granules (16.2 g) were added to low-substituted hydroxypropylcellulose (0.8 g), and the mixture was mixed in a glass bottle. The obtained mixture was tableted in an Autograph (manufactured by Shimadzu Corporation, AG-5000B) using a 9.5 mmϕ punch (tableting pressure: 7.5 KN/punch, weight per tablet: 398.3 mg) to give a plain tablet having the following composition. Then, the plain tablet was dried under reduced pressure at 40° C. for 16 hr.

Composition of Preparation (Per 398.3 mg)

| compound A | 50 mg |
| lactose | 254.6 mg |
| microcrystalline cellulose | 37.5 mg |
| hydroxypropylcellulose | 14.1 mg |
| monosodium fumarate | 23.4 mg |
| low-substituted hydroxypropylcellulose | 18.7 mg |
| Total | 398.3 mg |

Example 4

Compound A (71.13 g), cornstarch (18 g), purified sucrose (68.87 g), low-substituted hydroxypropylcellulose (40 g) and monosodium fumarate (28.33 g) were uniformly mixed to give a dusting powder for a drug-containing layer. Sucrose starch spherical granules (100 g) were fed into a centrifugal tumbling granulator (CF-mini, Freund Corporation), and the dusting powder for a drug-containing layer was dusted while spraying an aqueous solution of hydroxypropylcellulose (2 g) and monosodium fumarate (5 g) to give spherical granules. The obtained spherical granules were dried under reduced pressure at 40° C. for 16 hr, and passed through sieves to give 710-1180 μm granules.

Composition of Preparation (Per 100 mg)

| sucrose•starch spherical granule | 30 mg |
| compound A | 21.34 mg |
| cornstarch | 5.4 mg |
| purified sucrose | 20.66 mg |
| low-substituted hydroxypropylcellulose | 12 mg |
| hydroxypropylcellulose | 0.6 mg |
| monosodium fumarate | 10 mg |
| Total | 100 mg |

Example 5

Compound A (42.68 g), mannitol (217.32 g), microcrystalline cellulose (32 g) and monosodium fumarate (10 g) were uniformly mixed in a fluid bed granulator (Lab-1, POWREX CORPORATION), and the mixture was granulated while spraying an aqueous solution of hydroxypropylcellulose (12 g) and monosodium fumarate (10 g) and dried in the fluid bed granulator. The obtained granules were passed through 16 mesh sieves (aperture 1.0 mm) to give sieved granules. The obtained sieved granules (16.2 g) were added to low-substituted hydroxypropylcellulose (0.8 g), and the mixture was mixed in a glass bottle. The obtained mixture was tableted in an Autograph (manufactured by Shimadzu Corporation, AG-5000B) using a 6 mmϕ punch (tableting pressure: 3 KN/punch, weight per tablet: 170 mg) to give a plain tablet having the following composition. Then, the plain tablet was dried under reduced pressure at 40° C. for 16 hr.

Composition of Preparation (Per 170 mg)

| compound A | 21.34 mg |
| mannitol | 108.66 mg |
| microcrystalline cellulose | 16 mg |
| hydroxypropylcellulose | 6 mg |
| monosodium fumarate | 10 mg |
| low-substituted hydroxypropylcellulose | 8 mg |
| Total | 170 mg |

Example 6

Compound A (85.36 g), mannitol (155.64 g) and microcrystalline cellulose (30 g) were uniformly mixed in a fluid bed granulator (Lab-1, POWREX CORPORATION), and the mixture was granulated while spraying an aqueous solution of hydroxypropylcellulose (9 g) and sodium dihydrogen phosphate (20 g) and dried in the fluid bed granulator. The obtained granules were passed through 16 mesh sieves (aperture 1.0 mm) to give sieved granules. To the obtained sieved granules (250 g) were added croscarmellose sodium (12.5 g) and magnesium stearate (2.5 g), and they were mixed in a plastic bag. The obtained mixture was tableted by a rotary tableting machine (Correct 19K, Kikusui Seisakusho, Ltd.) using a 9.5 mmϕ punch (tableting pressure: 7.5 KN/punch, weight per tablet: 318 mg) to give a plain tablet having the following composition. Then, the plain tablet was dried under reduced pressure at 40° C. for 16 hr.

Composition of Preparation (Per 318 mg)

| | |
|---|---|
| compound A | 85.36 mg |
| mannitol | 155.64 mg |
| microcrystalline cellulose | 30 mg |
| hydroxypropylcellulose | 9 mg |
| sodium dihydrogen phosphate | 20 mg |
| croscarmellose sodium | 15 mg |
| magnesium stearate | 3 mg |
| Total | 318 mg |

Example 7

Compound A (85.36 g), mannitol (155.64 g), microcrystalline cellulose (30 g) and monosodium fumarate (20 g) were uniformly mixed in a fluid bed granulator (Lab-1, POWREX CORPORATION), and the mixture was granulated while spraying an aqueous solution of hydroxypropylcellulose (9 g) and dried in the fluid bed granulator. The obtained granules were passed through 16 mesh sieves (aperture 1.0 mm) to give sieved granules. To the obtained sieved granules (250 g) were added croscarmellose sodium (12.5 g) and magnesium stearate (2.5 g), and they were mixed in a plastic bag. The obtained mixture was tableted by a rotary tableting machine (Correct 19K, Kikusui Seisakusho, Ltd.) using a 9.5 mmϕ punch (tableting pressure: 7.5 KN/punch, weight per tablet: 318 mg) to give a plain tablet having the following composition. Then, the plain tablet was dried under reduced pressure at 40° C. for 16 hr.

Composition of Preparation (Per 318 mg)

| | |
|---|---|
| compound A | 85.36 mg |
| mannitol | 155.64 mg |
| microcrystalline cellulose | 30 mg |
| monosodium fumarate | 20 mg |
| hydroxypropylcellulose | 9 mg |
| croscarmellose sodium | 15 mg |
| magnesium stearate | 3 mg |
| Total | 318 mg |

Example 8

Compound A (85.36 g), mannitol (155.64 g) and microcrystalline cellulose (30 g) were uniformly mixed in a fluid bed granulator (Lab-1, POWREX CORPORATION), and the mixture was granulated while spraying an aqueous solution of hydroxypropylcellulose (9 g) and monosodium fumarate (20 g) and dried in the fluid bed granulator. The obtained granules were passed through 16 mesh sieves (aperture 1.0 mm) to give sieved granules. To the obtained sieved granules (250 g) were added croscarmellose sodium (12.5 g) and magnesium stearate (2.5 g), and they were mixed in a plastic bag. The obtained mixture was tableted by a rotary tableting machine (Correct 19K, Kikusui Seisakusho, Ltd.) using a 9.5 mmϕ punch (tableting pressure: 7.5 KN/punch, weight per tablet: 318 mg) to give a plain tablet having the following composition. Then, the plain tablet was dried under reduced pressure at 40° C. for 16 hr.

Composition of Preparation (Per 318 mg)

| | |
|---|---|
| compound A | 85.36 mg |
| mannitol | 155.64 mg |
| microcrystalline cellulose | 30 mg |
| hydroxypropylcellulose | 9 mg |
| monosodium fumarate | 20 mg |
| croscarmellose sodium | 15 mg |
| magnesium stearate | 3 mg |
| Total | 318 mg |

Example 9

Compound A (85.36 g), mannitol (166.64 g), microcrystalline cellulose (30 g) and monosodium fumarate (15 g) were uniformly mixed in a fluid bed granulator (Lab-1, POWREX CORPORATION), and the mixture was granulated while spraying an aqueous solution of hydroxypropylcellulose (9 g) and monosodium fumarate (5 g) and dried in the fluid bed granulator. The obtained granules were passed through 16 mesh sieves (aperture 1.0 mm) to give sieved granules. To the obtained sieved granules (155.5 g) were added microcrystalline cellulose (18.3 g), croscarmellose sodium (9.15 g) and magnesium stearate (1.65 g), and they were mixed in a plastic bag. The obtained mixture was tableted by a rotary tableting machine (Correct 19K, Kikusui Seisakusho, Ltd.) using a 9.5 mmϕ punch (tableting pressure: 7.5 KN/punch, weight per tablet: 369.2 mg) to give a plain tablet having the following composition. Then, the plain tablet was dried under reduced pressure at 40° C. for 16 hr.

Composition of Preparation (Per 369.2 mg)

| | |
|---|---|
| compound A | 85.36 mg |
| mannitol | 166.64 mg |
| microcrystalline cellulose | 66.6 mg |
| monosodium fumarate | 15 mg |
| hydroxypropylcellulose | 9 mg |
| monosodium fumarate | 5 mg |
| croscarmellose sodium | 18.3 mg |
| magnesium stearate | 3.3 mg |
| Total | 369.2 mg |

Example 10

Compound A (85.36 g), mannitol (166.64 g), microcrystalline cellulose (30 g) and monosodium fumarate (15 g) were uniformly mixed in a fluid bed granulator (Lab-1, POWREX CORPORATION), and the mixture was granulated while spraying an aqueous solution of hydroxypropylcellulose (9 g) and monosodium fumarate (5 g) and dried in the fluid bed granulator. The obtained granules were passed through 16 mesh sieves (aperture 1.0 mm) to give sieved granules. To the obtained sieved granules (155.5 g) were added calcium silicate (18.3 g), croscarmellose sodium (9.15 g) and magnesium stearate (1.65 g), and they were mixed in a plastic bag. The obtained mixture was tableted by a rotary tableting machine (Correct 19K, Kikusui Seisakusho, Ltd.) using a 9.5 mmφ punch (tableting pressure: 7.5 KN/punch, weight per tablet: 369.2 mg) to give a plain tablet having the following composition. Then, the plain tablet was dried under reduced pressure at 40° C. for 16 hr.

Composition of Preparation (Per 369.2 mg)

| compound A | 85.36 mg |
|---|---|
| mannitol | 166.64 mg |
| microcrystalline cellulose | 30 mg |
| monosodium fumarate | 15 mg |
| hydroxypropylcellulose | 9 mg |
| monosodium fumarate | 5 mg |
| calcium silicate | 36.6 mg |
| croscarmellose sodium | 18.3 mg |
| magnesium stearate | 3.3 mg |
| Total | 369.2 mg |

Example 11

Compound A (85.36 g), mannitol (161.64 g) and microcrystalline cellulose (30 g) were uniformly mixed in a fluid bed granulator (Lab-1, POWREX CORPORATION), and the mixture was granulated while spraying an aqueous solution of polyvinylpyrrolidone (18 g) and monosodium fumarate (5 g) and dried in the fluid bed granulator. The obtained granules were passed through 16 mesh sieves (aperture 1.0 mm) to give sieved granules. To the obtained sieved granules (250 g) were added croscarmellose sodium (12.5 g) and magnesium stearate (2.5 g), and they were mixed in a plastic bag. The obtained mixture was tableted by a rotary tableting machine (Correct 19K, Kikusui Seisakusho, Ltd.) using a 9.5 mmφ punch (tableting pressure: 7.5 KN/punch, weight per tablet: 318 mg) to give a plain tablet having the following composition. Then, the plain tablet was dried under reduced pressure at 40° C. for 16 hr.

Composition of Preparation (Per 318 mg)

| compound A | 85.36 mg |
|---|---|
| mannitol | 161.64 mg |
| microcrystalline cellulose | 30 mg |
| monosodium fumarate | 5 mg |
| polyvinylpyrrolidone | 18 mg |
| croscarmellose sodium | 15 mg |
| magnesium stearate | 3 mg |
| Total | 318 mg |

Example 12

Compound A (85.36 g) and mannitol (199.99 g) were uniformly mixed in a fluid bed granulator (Lab-1, POWREX CORPORATION), and the mixture was granulated while spraying an aqueous solution of hydroxypropylcellulose (9 g), fumaric acid (4.2 g) and sodium hydroxide (1.45 g) and dried in the fluid bed granulator. The obtained granules were passed through 16 mesh sieves (aperture 1.0 mm) to give sieved granules. To the obtained sieved granules (250 g) were added microcrystalline cellulose (25 g), croscarmellose sodium (12.5 g) and magnesium stearate (2.9 g), and they were mixed in a plastic bag. The obtained mixture was tableted by a rotary tableting machine (Correct 19K, Kikusui Seisakusho, Ltd.) using a 9.5 mmφ punch (tableting pressure: 7.5 KN/punch, weight per tablet: 348.5 mg) to give a plain tablet having the following composition. Then, the plain tablet was dried under reduced pressure at 40° C. for 16 hr.

Composition of Preparation (Per 348.5 mg)

| compound A | 85.36 mg |
|---|---|
| mannitol | 199.99 mg |
| hydroxypropylcellulose | 9 mg |
| fumaric acid | 4.2 mg |
| sodium hydroxide | 1.45 mg |
| microcrystalline cellulose | 30 mg |
| croscarmellose sodium | 15 mg |
| magnesium stearate | 3.5 mg |
| Total | 348.5 mg |

Example 13

Compound A (85.36 g) and mannitol (199.99 g) were uniformly mixed in a fluid bed granulator (Lab-1, POWREX CORPORATION), and the mixture was granulated while spraying an aqueous solution of hydroxypropylcellulose (9 g), fumaric acid (4.2 g) and sodium hydroxide (2.04 g) and dried in the fluid bed granulator. The obtained granules were passed through 16 mesh sieves (aperture 1.0 mm) to give sieved granules. To the obtained sieved granules (250.3 g) were added microcrystalline cellulose (25 g), croscarmellose sodium (12.5 g) and magnesium stearate (2.9 g), and they were mixed in a plastic bag. The obtained mixture was tableted by a rotary tableting machine (Correct 19K, Kikusui Seisakusho, Ltd.) using a 9.5 mmφ punch (tableting pressure: 7.5 KN/punch, weight per tablet: 349.1 mg) to give a plain tablet having the following composition. Then, the plain tablet was dried under reduced pressure at 40° C. for 16 hr.

Composition of Preparation (Per 349.1 mg)

| compound A | 85.36 mg |
|---|---|
| mannitol | 199.99 mg |
| hydroxypropylcellulose | 9 mg |
| fumaric acid | 4.2 mg |
| sodium hydroxide | 2.04 mg |
| microcrystalline cellulose | 30 mg |
| croscarmellose sodium | 15 mg |
| magnesium stearate | 3.5 mg |
| Total | 349.1 mg |

Example 14

Compound A (85.36 g) and mannitol (199.99 g) were uniformly mixed in a fluid bed granulator (Lab-1, POWREX CORPORATION), and the mixture was granulated while spraying an aqueous solution of hydroxypropylcellulose (9 g), fumaric acid (4.2 g) and sodium hydroxide (2.55 g) and dried in the fluid bed granulator. The obtained granules were passed through 16 mesh sieves (aperture 1.0 mm) to give sieved granules. To the obtained sieved granules (250.9 g) were added microcrystalline cellulose (25 g), croscarmellose sodium (12.5 g) and magnesium stearate (2.9 g), and they were mixed in a plastic bag. The obtained mixture was tableted by a rotary tableting machine (Correct 19K, Kikusui Seisakusho, Ltd.) using a 9.5 mmφ punch (tableting pressure: 7.5 KN/punch, weight per tablet: 349.6 mg) to give a plain tablet having the following composition. Then, the plain tablet was dried under reduced pressure at 40° C. for 16 hr.
Composition of Preparation (Per 349.6 mg)

| | |
|---|---|
| compound A | 85.36 mg |
| mannitol | 199.99 mg |
| hydroxypropylcellulose | 9 mg |
| fumaric acid | 4.2 mg |
| sodium hydroxide | 2.55 mg |
| microcrystalline cellulose | 30 mg |
| croscarmellose sodium | 15 mg |
| magnesium stearate | 3.5 mg |
| Total | 349.6 mg |

Example 15

Mannitol (190.99 g) was uniformly mixed in a fluid bed granulator (Lab-1, POWREX CORPORATION), and an aqueous solution of fumaric acid (4.2 g) and sodium hydroxide (1.45 g) was sprayed thereon. Compound A (85.36 g) was added thereto, and the mixture was granulated while spraying an aqueous solution of polyvinylpyrrolidone (18 g) and dried in the fluid bed granulator. The obtained granules were passed through 16 mesh sieves (aperture 1.0 mm) to give sieved granules. To the obtained sieved granules (250 g) were added microcrystalline cellulose (25 g), croscarmellose sodium (12.5 g) and magnesium stearate (2.9 g), and they were mixed in a plastic bag. The obtained mixture was tableted by a rotary tableting machine (Correct 19K, Kikusui Seisakusho, Ltd.) using a 9.5 mmϕ punch (tableting pressure: 7.5 KN/punch, weight per tablet: 348.5 mg) to give a plain tablet having the following composition. Then, the plain tablet was dried under reduced pressure at 40° C. for 16 hr.
Composition of Preparation (Per 348.5 mg)

| | |
|---|---|
| mannitol | 190.99 mg |
| fumaric acid | 4.2 mg |
| sodium hydroxide | 1.45 mg |
| compound A | 85.36 mg |
| polyvinylpyrrolidone | 18 mg |
| microcrystalline cellulose | 30 mg |
| croscarmellose sodium | 15 mg |
| magnesium stearate | 3.5 mg |
| Total | 348.5 mg |

Example 16

Compound A (106.7 g) and mannitol (242.4 g) were uniformly mixed in a fluid bed granulator (Lab-1, POWREX CORPORATION), and the mixture was granulated while spraying an aqueous solution of hydroxypropylcellulose (13.5 g), fumaric acid (2.5 g) and sodium hydroxide (0.863 g) and dried in the fluid bed granulator. The obtained granules were passed through 16 mesh sieves (aperture 1.0 mm) to give sieved granules. To the obtained sieved granules (183 g) were added microcrystalline cellulose (22.5 g), croscarmellose sodium (17.25 g) and magnesium stearate (2.25 g), and they were mixed in a plastic bag. The obtained mixture was tableted by a rotary tableting machine (Correct 19K, Kikusui Seisakusho, Ltd.) using a 6.0 mmϕ punch (tableting pressure: 2.5 KN/punch, weight per tablet: 90.0 mg) to give a plain tablet having the following composition. Then, the plain tablet was dried under reduced pressure at 40° C. for 16 hr.
Composition of Preparation (Per 90.0 mg)

| | |
|---|---|
| compound A | 21.34 mg |
| mannitol | 48.4875 mg |
| hydroxypropylcellulose | 2.7 mg |
| fumaric acid | 0.5 mg |
| sodium hydroxide | 0.1725 mg |
| microcrystalline cellulose | 9 mg |
| croscarmellose sodium | 6.9 mg |
| magnesium stearate | 0.9 mg |
| Total | 90.0 mg |

Example 17

Mannitol (349.1 g) was uniformly mixed in a fluid bed granulator (Lab-1, POWREX CORPORATION), and the mixture was granulated while spraying an aqueous solution of hydroxypropylcellulose (13.5 g), fumaric acid (2.5 g) and sodium hydroxide (0.863 g) and dried in the fluid bed granulator. The obtained granules were passed through 16 mesh sieves (aperture 1.0 mm) to give sieved granules. To the obtained sieved granules (91.5 g) and the sieved granules (91.5 g) of Example 16 were added microcrystalline cellulose (22.5 g), croscarmellose sodium (17.25 g) and magnesium stearate (2.25 g), and they were mixed in a plastic bag. The obtained mixture was tableted by a rotary tableting machine (Correct 19K, Kikusui Seisakusho, Ltd.) using a 6.0 mmϕ punch (tableting pressure: 2.5 KN/punch, weight per tablet: 90.0 mg) to give a plain tablet having the following composition. Then, the plain tablet was dried under reduced pressure at 40° C. for 16 hr.
Composition of Preparation (Per 90.0 mg)

| | |
|---|---|
| compound A | 10.67 mg |
| mannitol | 59.1575 mg |
| hydroxypropylcellulose | 2.7 mg |
| fumaric acid | 0.5 mg |
| sodium hydroxide | 0.1725 mg |
| microcrystalline cellulose | 9 mg |
| croscarmellose sodium | 6.9 mg |
| magnesium stearate | 0.9 mg |
| Total | 90.0 mg |

Example 18

Compound A (5999 g) and mannitol (13360 g) were uniformly mixed in a fluid bed granulator (FD-S2, POWREX CORPORATION), and the mixture was granulated while spraying an aqueous solution of hydroxypropylcellulose (756.0 g), fumaric acid (280.0 g) and sodium hydroxide (96.60 g) and dried in the fluid bed granulator. The obtained granules were pulverized using a powermill grinder (P-3, Showa Chemical Machinery) and a 1.5 mmϕ punching screen. To the obtained milled granules (36980 g) were added croscarmellose sodium (3478 g), microcrystalline cellulose (4536 g) and magnesium stearate (453.6 g), and they were mixed in a tumbler mixer (TM20-0-0 type, Suchiro Kakouki). The obtained mixture was tableted by a rotary tableting machine (AQUARIUS 36K, Kikusui Seisakusho, Ltd.) using a 9.5 mmϕ punch (tableting pressure: 6.8 KN/punch, weight per tablet: 360 mg) to give a plain tablet having the following composition. Then, the plain tablet was dried under reduced pressure at 40° C. for 16 hr.

Composition of Preparation (Per 360 mg)

| compound A | 85.36 mg |
|---|---|
| mannitol | 191.26 mg |
| hydroxypropylcellulose | 10.8 mg |
| fumaric acid | 4 mg |
| sodium hydroxide | 1.38 mg |
| croscarmellose sodium | 27.6 mg |
| microcrystalline cellulose | 36 mg |
| magnesium stearate | 3.6 mg |
| Total | 360 mg |

Comparative Example 1

Compound A (71.1 g) and mannitol (163.9 g) were uniformly mixed in a fluid bed granulator (Lab-1, POWREX CORPORATION), and the mixture was granulated while spraying an aqueous solution of hydroxypropylcellulose (9.0 g) and dried in the fluid bed granulator. The obtained granules were passed through 16 mesh sieves (aperture 1.0 mm) to give sieved granules. To the obtained sieved granules (230.0 g) were added croscarmellose sodium (17.6 g), microcrystalline cellulose (23.0 g) and magnesium stearate (2.3 g), and they were mixed in a plastic bag. The obtained mixture was tableted by a rotary tableting machine (Mini Rotary tableting machine, Kikusui Seisakusho, Ltd.) using a 9.5 mmϕ punch (tableting pressure: 6.5 KN/punch, weight per tablet: 360 mg) to give a plain tablet having the following composition. Then, the plain tablet was dried under reduced pressure at 40° C. for 16 hr.

Composition of Preparation (Per 360 mg)

| compound A | 85.36 mg |
|---|---|
| mannitol | 196.64 mg |
| hydroxypropylcellulose | 10.8 mg |
| croscarmellose sodium | 27.6 mg |
| microcrystalline cellulose | 36 mg |
| magnesium stearate | 3.6 mg |
| Total | 360 mg |

Comparative Example 2

Compound A (42.68 g), lactose (217.32 g), and microcrystalline cellulose (32 g) were uniformly mixed in a fluid bed granulator (Lab-1, POWREX CORPORATION), and the mixture was granulated while spraying an aqueous solution of hydroxypropylcellulose (12 g) and dried in the fluid bed granulator to give granules.

Composition of Granules (Per 152 mg)

| compound A | 21.34 mg |
|---|---|
| lactose | 108.66 mg |
| microcrystalline cellulose | 16 mg |
| hydroxypropylcellulose | 6 mg |
| Total | 152 mg |

Comparative Example 3

Compound A (42.68 g), lactose (217.32 g), and microcrystalline cellulose (32 g) were uniformly mixed in a fluid bed granulator (Lab-1, POWREX CORPORATION), and the mixture was granulated while spraying an aqueous solution of hydroxypropylcellulose (12 g) and dried in the fluid bed granulator. The obtained granules were passed through 16 mesh sieves (aperture 1.0 mm) to give sieved granules. The obtained sieved granules (15.2 g) were added to low-substituted hydroxypropylcellulose (0.8 g), and the mixture was mixed in a glass bottle. The obtained mixture was tableted in an Autograph (manufactured by Shimadzu Corporation, AG-5000B) using a 9.5 mmϕ punch (tableting pressure: 7.5 KN/punch, weight per tablet: 374.9 mg) to give a plain tablet having the following composition. Then, the plain tablet was dried under reduced pressure at 40° C. for 16 hr.

Composition of Preparation (Per 374.9 mg)

| compound A | 50 mg |
|---|---|
| lactose | 254.6 mg |
| microcrystalline cellulose | 37.5 mg |
| hydroxypropylcellulose | 14.1 mg |
| low-substituted hydroxypropylcellulose | 18.7 mg |
| Total | 374.9 mg |

Comparative Example 4

Compound A (42.68 g), mannitol (217.32 g), and microcrystalline cellulose (32 g) were uniformly mixed in a fluid bed granulator (Lab-1, POWREX CORPORATION), and the mixture was granulated while spraying an aqueous solution of hydroxypropylcellulose (12 g) and dried in the fluid bed granulator. The obtained granules were passed through 16 mesh sieves (aperture 1.0 mm) to give sieved granules. The obtained sieved granules (15.2 g) were added to low-substituted hydroxypropylcellulose (0.8 g), and the mixture was mixed in a glass bottle. The obtained mixture was tableted in an Autograph (manufactured by Shimadzu Corporation, AG-5000B) using a 6 mϕ punch (tableting pressure: 3 KN/punch, weight per tablet: 160 mg) to give a plain tablet having the following composition. Then, the plain tablet was dried under reduced pressure at 40° C. for 16 hr.

Composition of Preparation (Per 160 mg)

| compound A | 21.34 mg |
|---|---|
| mannitol | 108.66 mg |
| microcrystalline cellulose | 16 mg |
| hydroxypropylcellulose | 6 mg |
| low-substituted hydroxypropylcellulose | 8 mg |
| Total | 160 mg |

Experimental Example 1

The drug dissolution property of the dried plain tablets obtained in Example 1 and Comparative Example 1 was evaluated by a dissolution test (2.0 w/w % sodium dodecyl sulfate-containing phosphate buffer (pH 6.8), 900 mL, Paddle Method, 50 rpm, 37° C.). The dissolution test was performed according to the Japanese Pharmacopoeia 14th Edition Dissolution Test Method 2 (Paddle Method). The dissolution rate was measured by applying a test solution to a UV measurement apparatus (Agilent8453, Agilent) at each time point, quantifying compound A and the main decomposition product using Multi Component Analysis of the apparatus, and calculating the dissolution rate from the total amount thereof.

Figure 1:
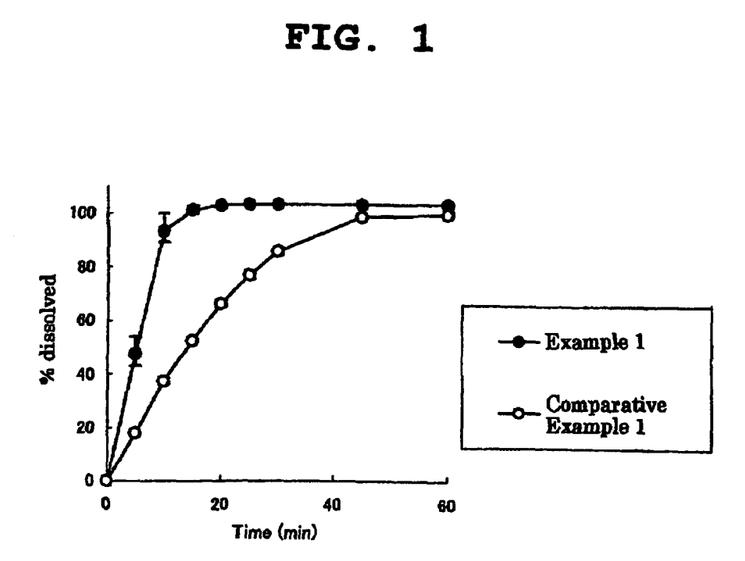
FIG. 1 shows the drug dissolution property of dried plain tablets obtained in Example 1 and Comparative Example 1.

The results are shown in FIG. 1, wherein -●- shows the results of the dried plain tablet of Example 1 and -○- shows the results of the dried plain tablet of Comparative Example 1.

As shown in FIG. 1, it was demonstrated that addition of a pH control agent improves dissolution property.

Experimental Example 2

The dried plain tablets obtained in Example 1 and Comparative Example 1 were placed in a glass bottle with a desiccant, respectively, and stored at 40° C. for one month. An increase in the amount of the decomposed product was measured by the following method.

Compound A was dissolved in an extract at about 1 μg/mL, and the solution was filtered using a non-aqueous filter (0.45 μm) and quantified by high performance liquid column chromatography (HPLC) under the following conditions.

HPLC conditions detector: ultraviolet absorption photometer, measurement wavelength: 240 nm column: YMC-Pack ProC18, 5 μm, inner diameter: 4.6 mm, length: 150 mm column temperature: 25° C.

mobile phase (A): 0.05 mol/L phosphate buffer (pH 3.0)/acetonitrile mixed solution (9:1)

mobile phase (B): 0.05 mol/L phosphate buffer (pH 3.0)/acetonitrile mixed solution (3:7)

flow: 1 mL/min gradient program (linear)

| time (min) | mobile phase (A) (%) | mobile phase (B) (%) |
|---|---|---|
| 0 (injecting) | 100 | 0 |
| 10 | 70 | 30 |
| 90 | 0 | 100 |
| 91 | 100 | 0 |
| 110 (injecting) | 100 | 0 |

The results are shown in Table 1. As shown in Table 1, it was demonstrated that addition of a pH control agent suppresses decomposition of compound A.

TABLE 1

| preparation | increase (%) in amount of decomposed product |
|---|---|
| tablet of Example 1 | 0.52 |
| tablet of Comparative Example 1 | 3.84 |

Experimental Example 3

The granules obtained in Example 2 and Comparative Example 2 were placed in a glass bottle with a desiccant, respectively, and stored at 40° C. for one month. An increase in the amount of the decomposed product was measured in the same manner as in Experimental Example 2.

The results are shown in Table 2. As shown in Table 2, it was demonstrated that addition of a pH control agent suppresses decomposition of compound A.

TABLE 2

| preparation | increase (%) in amount of decomposed product |
|---|---|
| granules of Example 2 | 0.10 |
| granules of Comparative Example 2 | 0.37 |

Experimental Example 4

The drug dissolution property of the dried plain tablets obtained in Example 3 and Comparative Example 3 was evaluated by a dissolution test (0.5 w/w % sodium dodecyl sulfate-containing phosphate buffer (pH 6.8), 900 mL, Paddle Method, 50 rpm, 37° C.). The dissolution test was performed according to the Japanese Pharmacopoeia 14th Edition Dissolution Test Method 2 (Paddle Method). The amount of dissolved drug was obtained by filtering the test solution with a membrane filter (pore size 0.45 μm) at each time point, and quantified by high-performance liquid column chromatography (HPLC) under the following conditions. The dissolution rate was calculated from the total amount of compound A (retention time about 10 min) and the main decomposition product (retention time about 4 min).

HPLC conditions detector: ultraviolet absorption photometer, measurement wavelength: 260 nm column: YMC-Pack ProC18, 5 μm, inner diameter: 4.6 mm, length: 150 mm column temperature: 25° C.

mobile phase: 0.05 mol/L phosphate buffer (pH3.0)/acetonitrile mixed solution (1:1)

flow: about 1 mL/min

Figure 2:
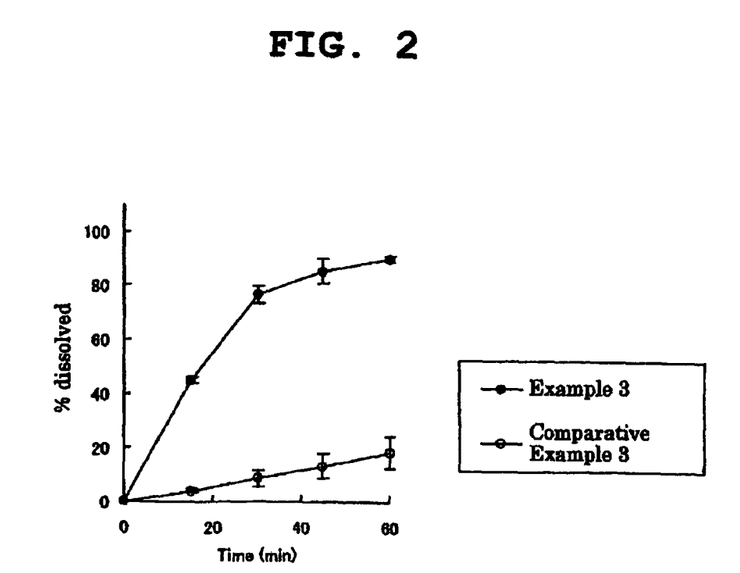
FIG. 2 shows the drug dissolution property of dried plain tablets obtained in Example 3 and Comparative Example 3.

The results are shown in FIG. 2, wherein -●- shows the results of dried plain tablet of Example 3 and -○- shows the results of dried plain tablet of Comparative Example 3.

As shown in FIG. 2, it was demonstrated that addition of a pH control agent improves dissolution property.

Experimental Example 5

The dried plain tablets obtained in Example 3 and Comparative Example 3 were placed in a glass bottle with a desiccant, respectively, and stored at 40° C. for one month. An increase in the amount of the decomposed product was measured in the same manner as in Experimental Example 2.

The results are shown in Table 3. As shown in Table 3, it was demonstrated that addition of a pH control agent suppresses decomposition of compound A.

TABLE 3

| preparation | increase (%) in amount of decomposed product |
|---|---|
| tablet of Example 3 | 1.31 |
| tablet of Comparative Example 3 | 3.83 |

Experimental Example 6

The drug dissolution property of the dried plain tablets obtained in Example 5 and Comparative Example 4 was performed according to Experimental Example 3. The results are shown in FIG. 3, wherein -●- shows the results of dried plain tablet of Example 5 and -○- shows the results of dried plain tablet of Comparative Example 4.

Figure 3:
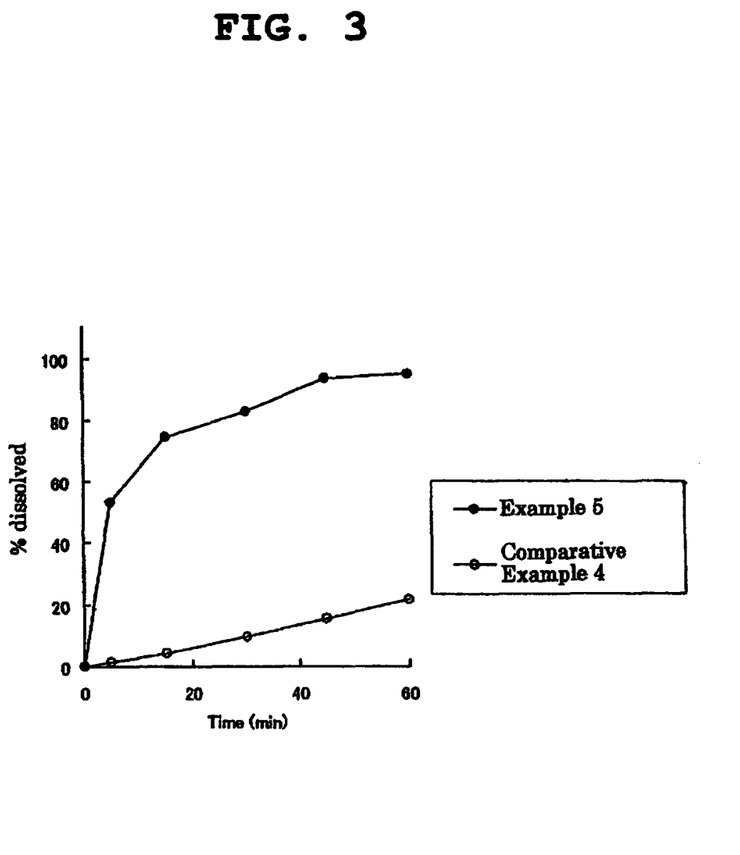
FIG. 3 shows the drug dissolution property of dried plain tablets obtained in Example 5 and Comparative Example 4.

As shown in FIG. 3, it was demonstrated that addition of a pH control agent improves dissolution property.

Experimental Example 7

The dried plain tablets obtained in Example 6 and Comparative Example 1 were placed in a glass bottle with a desiccant, respectively, and stored at 40° C. for one month. An increase in the amount of the decomposed product was measured in the same manner as in Experimental Example 2.

The results are shown in Table 4. As shown in Table 4, it was demonstrated that addition of a pH control agent showing optimal pH suppresses decomposition of compound A.

TABLE 4

| preparation | increase (%) in amount of decomposed product |
|---|---|
| tablet of Example 6 | 1.28 |
| tablet of Comparative Example 1 | 3.84 |

Experimental Example 8

The dried plain tablets obtained in Examples 12, 13 and 14 were placed in a glass bottle with a desiccant, respectively, and stored at 40° C. for two weeks. An increase in the amount of the decomposed product was measured in the same manner as in Experimental Example 2. The results are shown in Table 5. As shown in Table 5, it was demonstrated that addition of a pH control agent suppresses decomposition of compound A, and adjustment to an optimal pH increases the stability of compound A.

TABLE 5

| preparation | increase (%) in amount of decomposed product |
|---|---|
| tablet of Example 12 | 0.22 |
| tablet of Example 13 | 0.49 |
| tablet of Example 14 | 0.65 |

Experimental Example 9

The dried plain tablets obtained in Examples 16 and 17, and Comparative Example 1 were placed in a glass bottle with a desiccant, respectively, and stored at 40° C. for one month. An increase in the amount of the decomposed product was measured in the same manner as in Experimental Example 2.

The results are shown in Table 6. As shown in Table 6, the tablets of Example 16 and Example 17 showed a stabilizing effect.

TABLE 6

| preparation | increase (%) in amount of decomposed product |
|---|---|
| tablet of Example 16 | 0.56 |
| tablet of Example 17 | 0.84 |
| tablet of Comparative Example 1 | 3.84 |

Experimental Example 10

A pH control agent was dissolved or suspended in water at a concentration of 1% w/v at 25° C., and the resulting solution or suspension was measured for pH. The results are shown in Table 7.

TABLE 7

| pH control agent | ratio | pH (25° C.) |
|---|---|---|
| monosodium fumarate | | 3.57 |
| fumaric acid/sodium hydroxide | 7.487/2.583 | 3.56 |
| fumaric acid/sodium hydroxide | 6.816/3.311 | 4.07 |
| fumaric acid/sodium hydroxide | 6.242/3.790 | 4.64 |
| sodium dihydrogen phosphate | | 4.56 |

Experimental Example 11

Water (1080 mL) was added to three tablets of Comparative Example 1, and the mixture was stirred until complete disintegration of the tablets. The resulting suspension was measured for pH at 25° C. As a result, the pH was 8.02.

Experimental Example 12

The solubility of compound A in aqueous solutions with different pHs was measured as shown below.

An excess amount of compound A and an aqueous solution were placed in a test tube, and the mixture was shaken at 25° C. for 30 sec every 5 min. After 30 min, the solution was filtered with a 0.45 μm membrane filter to give a sample. Using the sample, the concentration of compound A was measured under the following HPLC conditions.

HPLC conditions
detector: ultraviolet absorption photometer,
measurement wavelength: 260 nm
column: YMC-Pack ProC18, 3 μm, inner diameter: 6 mm, length: 5 cm
column temperature: 25° C.
mobile phase: 0.05 mol/L phosphate buffer (pH 3.0)/acetonitrile mixed solution (1:1)
flow: about 1 mL/min

TABLE 8

| solution | solubility (mg/mL) |
|---|---|
| 0.1 mol/L HCl | less than 0.01 |
| pH 2.0 * | less than 0.01 |
| pH 3.0 * | less than 0.01 |
| pH 4.0 * | less than 0.01 |
| pH 5.0 * | less than 0.01 |
| pH 6.0 * | less than 0.01 |
| pH 7.0 * | 0.94 |

* Britton Robinson buffer

INDUSTRIAL APPLICABILITY

The solid pharmaceutical composition of the present invention shows both superior stability of compound (I) in a preparation, and superior dissolution property of the active ingredient from a preparation. Therefore, it is extremely useful as a preparation technique of pharmaceutical products.

While some of the embodiments of the present invention have been described in detail in the above, those of ordinary skill in the art can enter various modifications and changes to the particular embodiments shown without substantially departing from the novel teaching and advantages of the present invention. Such modifications and changes are encompassed in the spirit and scope of the present invention as set forth in the appended claims.

This application is based on U.S. provisional application No. 60/908,515, the contents of which are incorporated hereinto by reference.

The invention claimed is:

1. A solid pharmaceutical composition comprising a compound which is (5-methyl-2-oxo-1,3-dioxol-4-yl)methyl 2-ethoxy-1-{[2'-(5-oxo-4,5-dihydro-1,2,4-oxadiazol-3-yl) biphenyl-4-yl]methyl}-1H-benzimidazole-7-carboxylate potassium salt and a solid pH control agent which provides a pH of 3 to 5 when dissolved or suspended in water at a concentration of 1% w/v at 25° C.

2. The pharmaceutical composition of claim 1, wherein the pH control agent is monosodium fumarate or a combination of fumaric acid and sodium hydroxide.

3. A method of stabilizing a compound which is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt in a solid pharmaceutical composition or improving dissolution of a compound which is (5-methyl-2-oxo-1,3-dioxol-4-yl)methyl 2-ethoxy-1-{[2'-(5-oxo-4,5-dihydro-1,2,4-oxadiazol-3-yl) biphenyl-4-yl]methyl}-1H-benzimidazole-7-carboxylate potassium salt from a solid pharmaceutical composition, which comprises adding a pH control agent having a pH of 3 to 5 when dissolved or suspended in water at a concentration of 1% w/v at 25° C. to the solid pharmaceutical composition comprising the compound.

* * * * *